(12) United States Patent
Ziarati

(10) Patent No.: US 9,787,750 B2
(45) Date of Patent: Oct. 10, 2017

(54) UNIVERSAL INTERFACE SYSTEM FOR MRI APPLICATIONS

(71) Applicant: Resonance Technology, Inc., Northridge, CA (US)

(72) Inventor: Mokhtar Ziarati, Porter Ranch, CA (US)

(*) Notice: Subject to any disclaimer, the term of this patent is extended or adjusted under 35 U.S.C. 154(b) by 323 days.

(21) Appl. No.: 14/142,414

(22) Filed: Dec. 27, 2013

(65) Prior Publication Data

US 2015/0200996 A1   Jul. 16, 2015

Related U.S. Application Data

(63) Continuation-in-part of application No. 13/725,339, filed on Dec. 21, 2012, now Pat. No. 9,571,820.

(60) Provisional application No. 61/748,423, filed on Jan. 2, 2013, provisional application No. 61/729,457, filed on Nov. 23, 2012, provisional application No. 61/582,323, filed on Dec. 31, 2011.

(51) Int. Cl.
| | |
|---|---|
| H04L 29/08 | (2006.01) |
| H04L 12/28 | (2006.01) |
| A61B 5/055 | (2006.01) |
| H05K 9/00 | (2006.01) |
| A61B 5/00 | (2006.01) |
| H04N 13/04 | (2006.01) |

(52) U.S. Cl.
CPC ............ *H04L 67/02* (2013.01); *A61B 5/0046* (2013.01); *A61B 5/055* (2013.01); *H04L 12/2838* (2013.01); *H05K 9/0054* (2013.01); *H04N 13/0434* (2013.01); *H04N 2213/001* (2013.01)

(58) Field of Classification Search
CPC ... H04L 12/2838; H04L 67/02; H05K 9/0054; H04N 13/0434; H04N 2213/001; A61B 5/0046; A61B 5/055
See application file for complete search history.

(56) References Cited

U.S. PATENT DOCUMENTS

| | | | |
|---|---|---|---|
| 5,412,419 A | 5/1995 | Ziarati | |
| 5,432,544 A | 7/1995 | Ziarati | |
| 5,627,902 A | 5/1997 | Ziarati | |
| 5,733,247 A | 3/1998 | Fallon | |
| 5,877,732 A | 3/1999 | Ziarati | |
| 6,229,311 B1 | 5/2001 | Abenaim | |
| 6,961,604 B1 | 11/2005 | Vahasalo | |
| 7,746,072 B2* | 6/2010 | Van Helvoort | G01R 33/3415 324/309 |
| 8,214,012 B2 | 7/2012 | Zuccolotto et al. | |
| 8,735,723 B2 | 5/2014 | Jiang et al. | |
| 2005/0273000 A1* | 12/2005 | Dinehart | G01R 33/283 600/410 |

(Continued)

*Primary Examiner* — Christopher S Kelley
*Assistant Examiner* — Maria Vazquez Colon
(74) *Attorney, Agent, or Firm* — Larry K. Roberts

(57) ABSTRACT

An interface system for providing a signal interface between devices in a magnetic resonance imaging (MRI) magnet room and devices in the outside environment to the magnet room. An exemplary embodiment includes a signal transmission link between the MRI magnet room and the outside environment, the link including a wireless local area network. A controller system is located in the outside environment and connected to the devices in the outside environment. A transducer system is located in the MRI magnet room and connected to the devices in the MRI magnet room.

15 Claims, 12 Drawing Sheets

(56) References Cited

U.S. PATENT DOCUMENTS

| | | | |
|---|---|---|---|
| 2009/0276515 A1* | 11/2009 | Thomas | G06F 19/327 709/223 |
| 2010/0231483 A1* | 9/2010 | Bazih | G01R 33/283 345/8 |
| 2010/0308826 A1 | 12/2010 | Saes et al. | |
| 2012/0013525 A1 | 1/2012 | Trcka et al. | |

* cited by examiner

UNIVERSAL INTERFACE SYSTEM FOR MRI APPLICATIONS

CROSS-REFERENCE TO RELATED APPLICATIONS

This application claims priority from U.S. Provisional Application No. 61/748,423, filed Jan. 2, 2013, and is a continuation-in-part of U.S. application Ser. No. 13/725,339, filed Dec. 21, 2012, which in turn claimed priority from U.S. Provisional Application 61/729,457, filed Nov. 23, 2012, and from U.S. Provisional Application 61/582,323, filed Dec. 31, 2011, the entire contents of which applications are hereby incorporated by reference.

BACKGROUND

The use of displays in a Magnetic Resonance Imaging (MRI) equipment environment was first developed in the late 80's and early 90's, as described in U.S. Pat. Nos. 5,412,419, 5,432,544, 5,627,902, and 5,877,732.

MRI is one of the fastest changing imaging modalities in the world. In addition to the use of MRI for the diagnostic purpose, other applications such as fMRI have been a major use of this imaging modality. The fMRI field requires various stimulation tasks such as an auditory and visual delivery system along with eye tracking to record the movements of the eyes during the procedure. There is also a need to have an easy method of linking the subject to the outside world. With current technology, there is no easy method of have different devices interfaced in the magnet room. For the time being, various devices like response, button, auditory, video and other equipment are made by different vendors and there is not an easy way of using them as a unit. For example, if the subject is being scanned and the stimulation tasks include creating a virtual reality world for the subject and recording both the subject's eye movements and hand movements, or recording the facial expression, or simply communicating with the patient during the procedure, at least four to five different vendor products might be involved. Synchronizing the various products together is not an easy task. All of these tasks are not universal and often are difficult to perform.

BRIEF DESCRIPTION OF THE DRAWINGS

Features and advantages of the disclosure will readily be appreciated by persons skilled in the art from the following detailed description when read in conjunction with the drawing wherein:

FIG. 3A illustrates features within circle 3A of FIG. 3.

DETAILED DESCRIPTION

Figure 1:
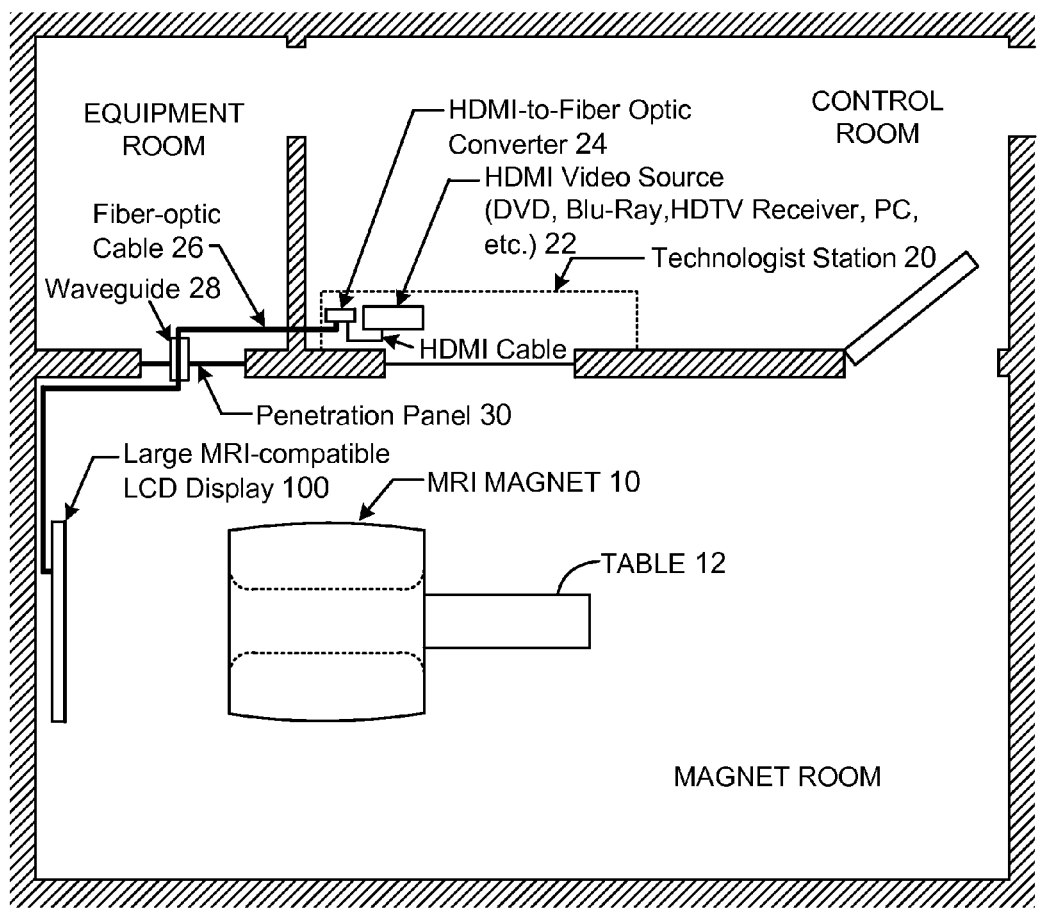
FIG. 1 is a schematic illustration of a 3D LCD monitor setup in an MRI suite.

In the following detailed description and in the several figures of the drawing, like elements are identified with like reference numerals. The figures are not to scale, and relative feature sizes may be exaggerated for illustrative purposes.

A 3D TV and the human eye have a lot in common. Since our eyes are spaced slightly apart, the left and right eye sees images from a slightly different perspective. The human brain then combines the two images to create a 3D impression. A 3D TV works the same way. Two images—displayed from slightly different angles—are viewed through 3D glasses and then combined by the brain to construct a 3D image The first generation of 3D shutter glasses produced a 3D effect, in part, with technology embedded in the glasses. 3D shutter glasses function just like a camera shutter. A 3D television, in synchronization with the 3D glasses, alternately flashes a 2D image to each eye through a liquid crystal layer embedded within each lens of the glasses. The viewer's brain then combines the images flashed to each eye to create a 3D effect. However, the use of 3D shutter glasses in an MRI magnet room application is useless due to the electronics and battery existing in the active shutter glasses.

The next generation FPR (Film Patterned Retarder) 3D relies on technology embedded in the television. FPR 3D glasses use a circular polarized filter to present two images concurrently to each eye. FPR 3D TVs incorporate the FPR technology in which a polarized film is placed on the 3D television screen to effectively split the left and right images into interweaving odd and even lines onscreen, and along with the 3D glasses which use circular polarization filters of opposite sense, separates the left and right images before they are delivered to the brain. This technically halves the original resolution of 3D content to each eye. The images are then combined by the brain to create the 3D impression. The applicant has recognized that this technology is ideal for use in MRI applications.

An LCD TV can be shielded to block the emission of electromagnetic interference (EMI) inside of the MRI room, to provide an MRI-compatible display. For example, the front active part of the LCD TV may be shielded with a micro conductive mesh or laser aided conductive mesh which is 30 micrometers thick and will not appear when viewed with the naked eye. The entire LCD monitor will then be housed in a shielded Faraday cage, with inputs for power and the video/audio signals (e.g. carried by fiber optics or by wireless signals on a wireless local area network (WLAN), such as a Wi-Fi network). As used herein, WLAN and Wi-Fi network are used synonymously.

FIG. 1 illustrates a typical component layout within the MRI suite. In this exemplary layout, the MRI magnet is disposed in the magnet room, with a patient table for positioning the patient in the bore of the MRI magnet 10. An MRI-compatible 3D display such as a large MRI-compatible LCD display 100 is positioned on a wall in the magnet room at a position selected to allow the patient in the MRI bore to observe the display, with the aid of a mirror. In this exemplary embodiment, the MRI-compatible 3D display is a display 100 which employs FPR technology to provide a 3D effect when used with an appropriate set of goggles or glasses, with circular polarization filters of opposite sense through which the image generated by the 3D display is viewed.

The control room includes the Technologist Station 20 for controlling the MRI system. An FPR-compatible video source 22 capable of generating signals to produce the 3D image is placed in the control room, and its signal is converted (e.g. through an HDMI-to-Fiber Optic Converter 24) to an optical signal carried on an optical fiber 26. The video source may be, for example, a DVD player, HDTV receiver, a PC, etc. The optical fiber is passed from the control room into the equipment room and through a waveguide 28 positioned in an RF shield wall with a penetration panel, collectively shown as 30 in FIG. 1, to the magnet room and to the large MRI-compatible LCD display 100. Alternatively, in another embodiment, the video source signals may be broadcast using a Wi-Fi broadband network or WLAN, wherein a Wi-Fi repeater is used to transmit signals (e.g. from an antenna mounted to the magnet room wall).

Figure 2:
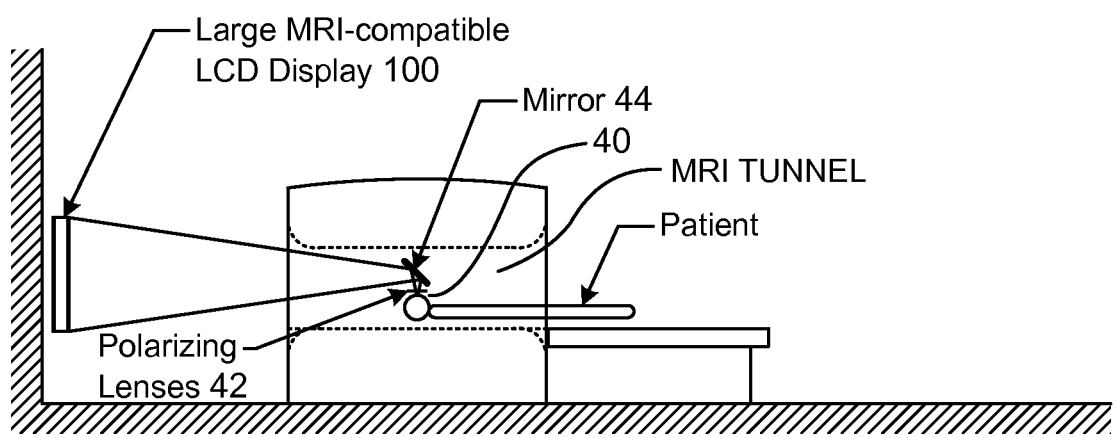
FIG. 2 is a diagrammatic cross-sectional view of an exemplary embodiment of a system for 3D display delivery in the MRI.

FIG. 2 illustrates the patient setup for the system in further detail. The patient wears the circular polarized passive glasses or goggles 40, with lenses 42 having circular polarization filters of opposite polarization sense for the left and right eye, typically applied by a filter film, and through the use of a reflective mirror 44, can view the 3D MRI-compatible display (e.g. a shielded 3D LCD TV) located on either end of the MRI bore (tunnel). The patient goggles 40 are configured to be MRI-compatible and fabricated without magnetic materials. Alternatively the circularly polarized filters can be built into the passive goggles or applied to the mirror 44 into which the patient looks to see the display image. The patient goggles are typically fabricated of a very thin layer of optically clear plastic on which the filters are formed, and, because of the thinness, do not affect substantially the 3D image quality.

In exemplary embodiments, the display 100 may be a large screen high definition 3D display or TV, utilizing LCD, LED or OLED technology (i.e. a 3D HD TV) and images generated by the display are relayed to the subject via a reflective mirror applied to a rear surface of a substrate formed of optically isotropic material. Alternatively, this could be a front surface mirror.

In an exemplary embodiment for use in an MRI magnet room, the 3D TV is housed in a non-magnetic Faraday cage to shield EMI. A clear conductive window overlay is specially made for the MRI 3D application utilizing FR technology, where it is optically clear or transparent and does not affect screen polarization.

The process of making the conductive window for the display in one exemplary embodiment uses a very fine conductive mesh laminated between two layers of optically isotropic glass or plastic material in a way that the edge of the mesh at the window edges is exposed. A conductive adhesive such as silver epoxy is applied to the mesh and window edges. By applying the silver epoxy, all the window edges become shorted to the mesh, increasing a surface area of conductive material in electrical contact with the mesh.

With the conductive window assembled in the housing, the edge of the conductive window stays in tight contact with the housing of the display. For the 3D system to operate properly, the base material of any adhesive or other structures used to build the window may not cause interference with the polarization of the TV. Optically isotropic materials are used for the rf (radio frequency) conductive window on the display and the reflective mirror (i.e. materials having the same optical properties in all directions). The mesh may be sandwiched between the two layers of the window because the mesh is very fine and to protect it from damage.

Another alternative for constructing the fine mesh is to start with a sheet of conductive copper applied to a glass layer, and then etch away most of the copper, leaving only a very fine line in the shape of very fine mesh. The etching may be done by a laser or other etching techniques.

Figure 3:
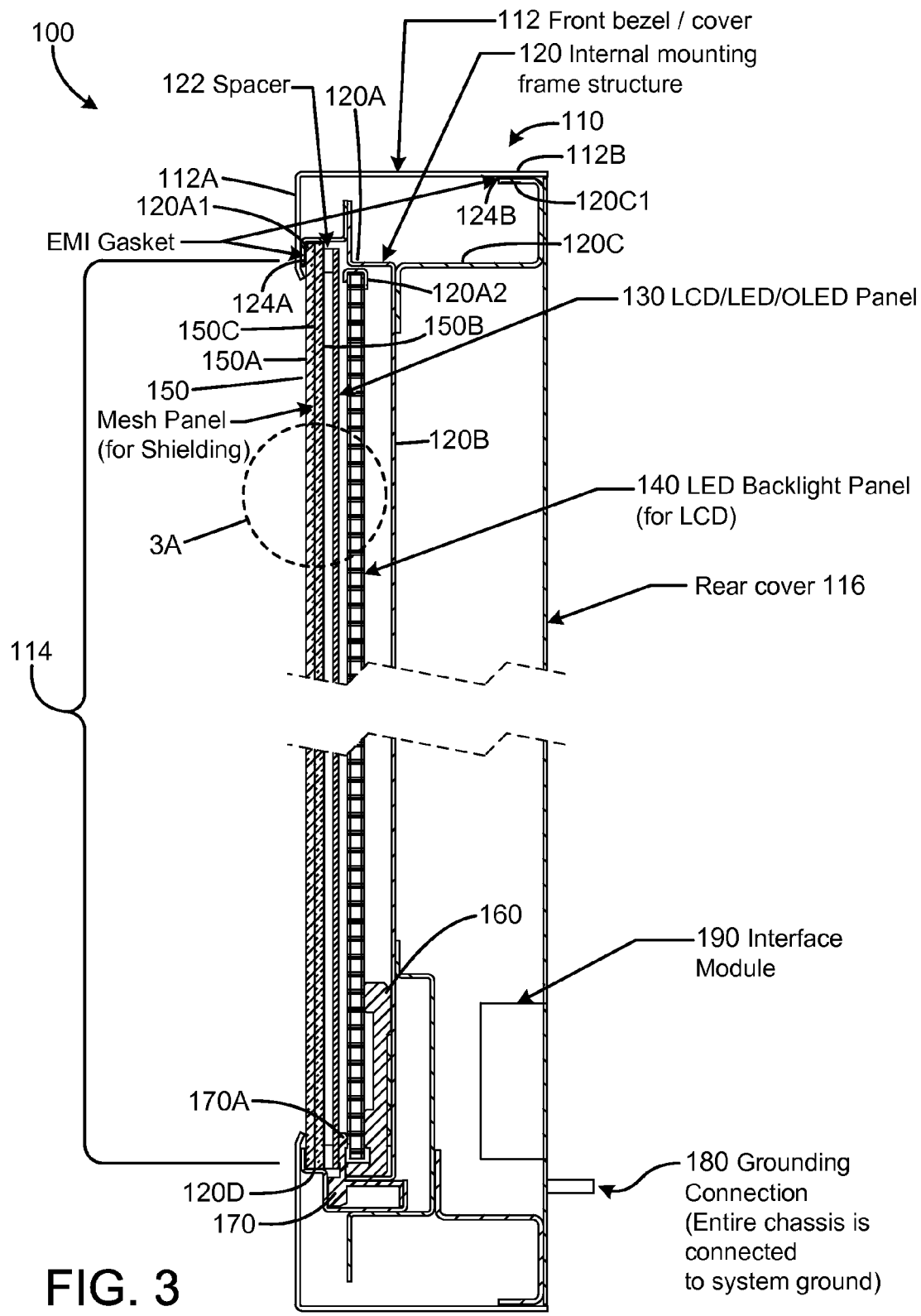
FIGS. 3 and 3A are cross-sectional diagrammatic illustrations of an exemplary embodiment of a 3D display.
Figure 3A:
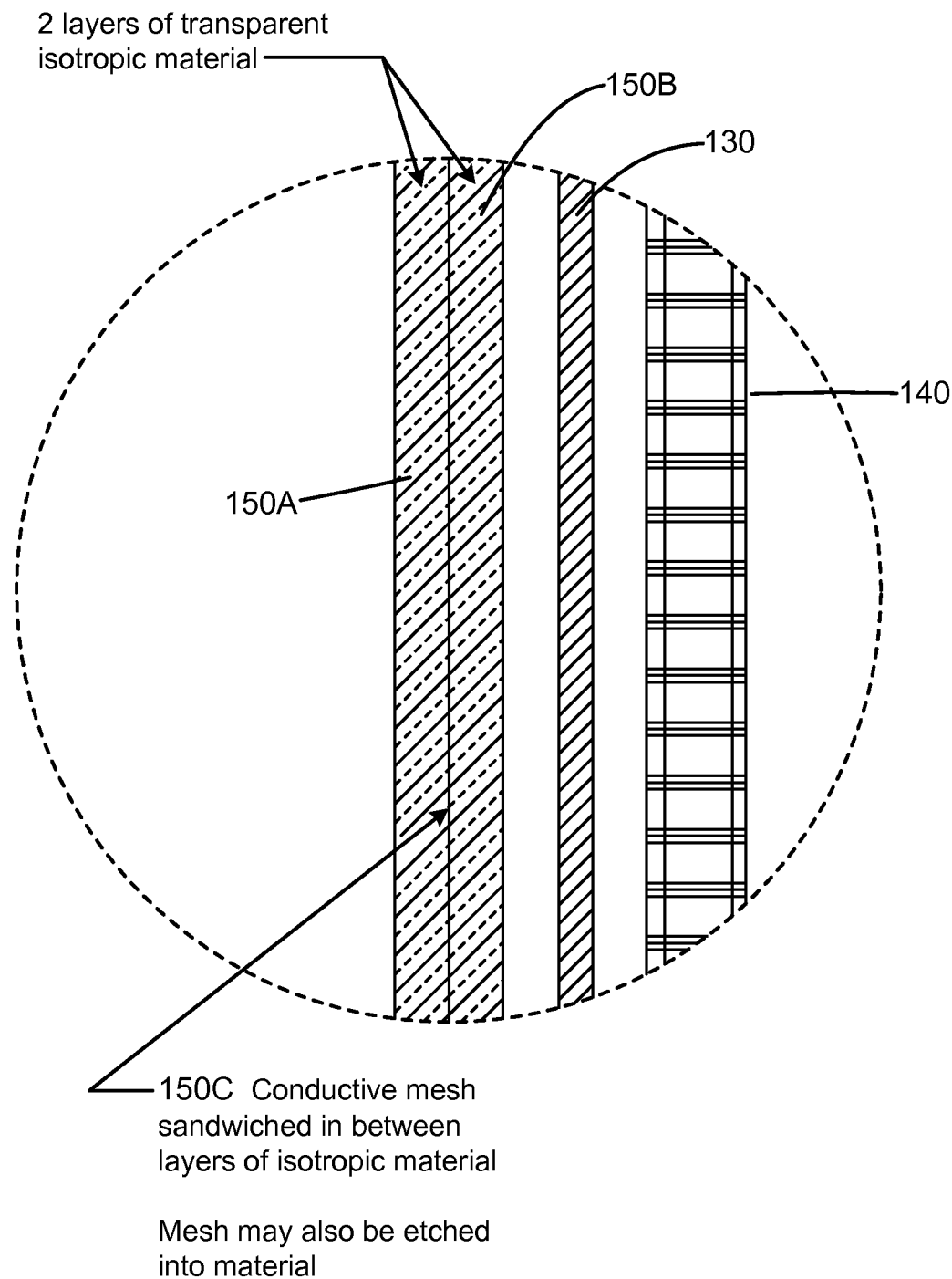

FIG. 3 is a diagrammatic cross-sectional view illustrating features of an exemplary embodiment of a 3D flat panel display 100 suitable for use in the magnet room environment of FIGS. 1 and 2. The display is constructed to provide a Faraday cage 110 defined by non-magnetic, electrically conductive materials. The Faraday cage 110 includes a front bezel or cover structure 112 which circumscribes the display panel area 114, and rear cover 116. The cover structure 112 may be fabricated of a non-magnetic electrically conductive material such as, by way of example only, brass or aluminum. The rear cover 116 attaches to the back of the cover structure 112. The Faraday Cage 110 includes an internal mounting frame structure 120 which is positioned between the inside of the front bezel portion 112A of the cover structure 112 and the rear cover 116. The rear cover and the internal mounting frame structure are also fabricated of non-magnetic electrically conductive material, such as brass or aluminum.

The internal mounting frame structure 120 and the cover structure 112 are configured to support the planar display system components, including the LCD/LED/OLED display panel 130, an LED backlight panel 140 (for an LCD implementation), and a mesh panel assembly 150 to cover the display panel or window area 114. The display panel may be a flat panel display such as an LCD (liquid crystal display) panel, an LED (light emitting diode) panel, an OLED (organic light emitting diode) panel, or even a plasma panel, for example. In the case of an LCD display panel, the backlight panel 140 is provided behind the display panel 130. The backlight panel 140 may be omitted for the implementation in which the display panel is OLED.

The mesh panel assembly 150 in this exemplary embodiment includes planar layers 150A and 150B of transparent optically isotropic material, such as a glass, which sandwich a non-magnetic, electrically conductive mesh 150C. The opening size of the mesh is preferably sufficiently small so as to block RF signals from passing through, yet large enough to allow the optical image rays pass through. An exemplary mesh opening size is on the order of 50 mesh openings per square inch. The mesh may be fabricated from copper, tungsten or alloy thereof, for example. The mesh panel assembly 150 is constructed to be optically isotropic, i.e. with a refractive index not dependent on the polarization and propagation direction of light. If the mesh panel assembly 150 were to be anisotropic, and exhibit birefringence, this could affect the polarized light emitted from the panel 130 and destroy the 3D effect. The panel 150 could also be a single layer of optically isotropic material, on which the mesh is applied or etched. However, to protect the mesh from damage, sandwiching the mesh between two layers can be advantageous. High quality isotropic glass, and plastics such as isotropic acrylic and CR39, may be employed to form the window assembly 150.

In this exemplary embodiment, the display panel 130 is spaced from the mesh panel assembly 150 by an elastomeric spacer member 122. An EMI (electromagnetic interference) gasket 124A is positioned between adjacent surfaces of the edge of the mesh panel 150 and the inner surface of flange portion 120A1 of the internal mounting frame structure 120. Another EMI gasket 124B is positioned between adjacent portions of the back edge 112B of the cover structure 112 and the back flange portion 120C1 of the internal mounting frame structure 120. The EMI gaskets can be fabricated of a springy non-magnetic, electrically conductive material, such as a copper/bronze alloy or beryllium copper.

The edges of the electrically conductive mesh layer 150C are brought into contact with the adjacent surface of the internal mounting frame structure 120, e.g. at 120D, so that the mesh is electrically connected to the internal mounting frame structure 120. A grounding connection 180 at the rear cover is connected to system ground within the magnet room so that the Faraday cage 110 is grounded.

A support structure 160 is positioned between a back panel portion 120B of the internal mounting frame structure 120 and the lower portion of the LED backlight 140. The support structure 160 is fabricated of a non-magnetic material such as aluminum. The top edge of the LED backlight is secured by a bracket portion 120A2 of the frame structure 120. A circuit board structure 170 is positioned with an upwardly extending board portion 170A positioned between the display panel 130 and the backlight panel 140. The board portion can include circuit traces for making electrical contact with the circuit of the display panel, for example. The particular technique for fabricating the display panel 130 and driving it to provide the 3D display images may be conventional.

An interface module 190 is positioned within the Faraday cage, adjacent the rear cover 116, and provides a power supply for the 3D flat panel display 100, and a connection (e.g. fiber optic, broadband Wi-Fi) for the video source signals to be supplied to the 3D flat panel display 100.

The 3D flat panel display 100 in this exemplary embodiment employs FPR technology to provide a 3D effect when used with an appropriate set of goggles or glasses, with circular polarization filters of opposite sense through which the image generated by the 3D display is viewed. Alternatively, the display could use left and right linear polarizations to produce the 3D effects, with corresponding left and right linear polarization on the polarized films applied to the goggles worn by the patient. Other display technologies could produce the 3D effect in conjunction with electronics to create the 3D effect on the display itself, without the need for the patient to wear polarized glasses. For example, parallax barrier, glasses-free displays are known, which work by placing an opaque screen door-like barrier over the screen. Each eye views the barrier from a slightly different angle, and therefore sees different sets of pixels behind it. Some manufactures use an LCD barrier that can be turned off to enable 2D viewing. In the case of the parallax barrier, glasses-free display, the patient might directly view the 3D image reflected from the mirror. In all cases, the optical path between the image panel generating the 3D images and the patient's eyes should not pass through birefringent materials, which may adversely affect the 3D content of the images.

Figure 4:
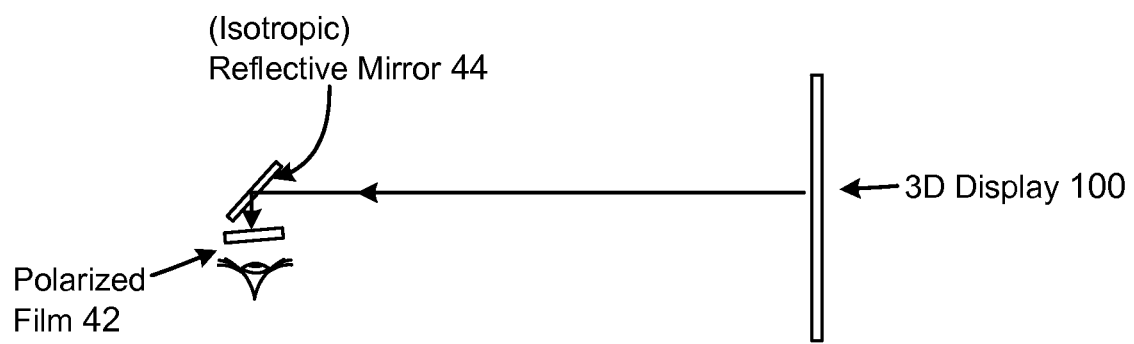
FIG. 4 is a diagrammatic depiction of a patient viewing a 3D display while lying in an MRI bore.

FIG. 4 diagrammatically illustrates how, in one exemplary embodiment, a patient in an MRI tunnel could view the 3D images generated by the 3D flat panel display 100. The patient wears the circular polarized passive glasses or goggles, with lenses having circular polarization filters of opposite polarization sense for the left and right eye, typically applied by a filter film, and through the use of a reflective mirror, can view the MRI-compatible display, e.g. a shielded LCD TV, located on either end of the MRI bore (tunnel). The glasses are configured to be MRI-compatible, without magnetic materials. Alternatively the circularly polarized filters can be built into the passive glasses or applied to the mirror which the patient looks into to see the display image. The patient can see the display while lying down on the MRI bore, using the combination of the polarized films in conjunction with the reflective mirror.

The reflective mirror 44 in the MRI bore is optically isotropic, i. e. with a refractive index not dependent on the polarization and propagation direction of light. Typically, the reflective surface is placed on a back side of the mirror substrate, to reduce chances of scratching or damaging the reflective surface (as compared to forming the reflective surface on the front face of the mirror substrate). A suitable exemplary plastic for the mirror substrate is acrylic or CR39. For the case in which the reflective surface is placed on the back surface of the mirror substrate, the light path is through the substrate, which in this case should be formed of an optically isotropic plastic material, to avoid affecting the 3D image content of the viewed image. If the reflective surface is placed on the mirror front face, then the light path does not pass through the mirror substrate, and the substrate material should have little effect on the image quality.

In another aspect of the invention, an interface system is provided, to interface between the outside environment and the MRI magnet room so the user can, in an exemplary embodiment, plug and play different modules as the need arises. For example, in one particular application, realistic 3D video can be delivered to the person undergoing an MRI exam or performing any complex fMRI task. This television/monitor with an interface may help the clinical claustrophobic patients to finish their exam with no need for sedation and also enable the scientist for the first time to run more complex and realistic tasks in 3D in the virtual world to the patients.

Following is an exemplary list of some of the tools the scientist and/or clinician can use in the MRI room while scanning the patients:

a) Present auditory tones with wide frequency range in audio spectrum.

b) Provide a clear communication system and be able to record the subject's verbal response during the MRI procedure.

c) Provide a camera to monitor of the eye movements or simply observe the patients while being scanned.

d) Present a 3D video/still image to the subject.

e) Provide different interfaces from the magnet room to the control room for such devices as, joystick, trackball, keyboard, writing pad, music keyboard, response key, force measurement, camera, eye tracker, and similar devices. The interfaces may include USB/HDMI/Serial/Parallel/VGA ports.

There are currently more than 20,000 MRI systems installed in the world. To install any devices in the pre-existing facility requires some complex tasks and in some cases may be very time consuming, if possible at all. Any devices installed in the magnet room that carry signals through wire have to be linked to the outside through a low pass filter. Because the magnet room is a Faraday's cage, no radio frequencies (RF) in the range of the MRI operating frequency should be leaked in the magnet room.

The interface system described more fully below is configured to provide a universal interface between the control room and magnet room. By "universal" interface is meant an interface system that can interface between devices in the MRI magnet room and devices in the control room, including, for example, devices which employ different signal interfaces, or signal protocols, or which may be provided by different vendors. One exemplary embodiment of the interface system uses FPGA (field programmable gate array) technology to provide very powerful capabilities to the user. Exemplary embodiments of the interface system are illustrated in FIGS. 5-11.

In order to calculate the necessary bandwidth to transmit the video via a WLAN such as a Wi-Fi network, the following calculation can be performed.

f=Bp where f=frequency, B is the magnetic field, and p=42.576 is Gyromagnetic constant for Hydrogen H1 (Larmor constant).

Frequency of the MRI=magnetic field*42.576 Mhz per Tesla.

The most common MRI field strength is 1.5 Tesla which means the frequency is about 63.864 Mhz. In the newer magnets used for the patients, 3 Tesla has become the standard the past few years. There are other magnets up to 11 Tesla used for research purposes only and the frequency of the operation is 11*42.5=467 MHz. The frequency ranges from a few MHz to 500 MHz, so the system cannot introduce any EMI noise in this range in the magnet room otherwise it will cause artifacts on the MRI images taken from the patients.

To simplify the installation of a device using the interface system, the operator preferably can plug in the device and immediately use the product. In an exemplary embodiment, a 5.8 GHz transceiver may be used to send the video and all the information to the MRI scan room and vice versa without using any signal cables between the MRI scan room and the control room. Transceivers are currently being used in many applications operating at this frequency range. In the future, transceiver equipment with much higher bandwidths may become available and may also be useful in the disclosed interface system.

The following formula is to calculate the bandwidth necessary to transmit the HDMI data along with other control signals via Wi-Fi:

BW=TV resolution*number of color (3Byte per color)*refresh rate.

BW=1920×1080×24×60=3 Ghz

Therefore 5.8 GHz is sufficient to broadcast a full color HDMI signal. The system will include an rf antenna 302, 402 placed on both sides of the filter or penetration panel 30 between the magnet room and the outside environment, typically a control room, using a feed through plug to act as a repeater for broadcasting Wi-Fi signals into the magnet room, and for receiving signals from the magnet room.

As a backup system in case there is an issue with the Wi-Fi portion of the modules, a fiber optic signal transmission link 26 between the two rooms may be provided. The electronics module in the magnet room can be powered using a lead acid battery or compatible non-magnetic rechargeable battery. In an exemplary embodiment of the system, the power is connected to the control room module and a linear power supply may be used to do the same in the magnet room.

The interface system includes two transceiver modules 330, 430 as shown in FIGS. 5-11.

Magnet Room Devices: In the embodiment illustrated in FIG. 5, the MRI system includes several exemplary devices in the magnet room:

1) 3D HDTV 304: Large Screen High Definition 3D TV or display, utilizing LED, LCD or OLED technology to relay the image to the subject via reflective mirror applied to Isotropic material. This could be a front surface mirror applied on the glasses or compatible material that does not affect the polarization of the wave from 3D TV. The 3D HDTV is housed in a non-magnetic Faraday cage to shield EMI, as described above regarding the embodiment of FIGS. 3-4. The clear conductive window overlay is specially made for the application where it is optically clear and does not affect screen polarization. In this example, the HD TV includes an HDMI wireless receiver to receive wireless data signals.

2) Wi-Fi Transmitter 306: This provides a wireless method of high definition video transmission suited for large screen HD TVs.

3) Wi-Fi 308: This is configured to provide high bandwidth wireless data transmission for the example operating frequency at 5.8 Ghz.

4) Patient Monitoring Camera 310: This may be a high resolution camera used to monitor the subject while being scanned. The camera has a non-magnetic construction and housed in a faraday cage type of housing to prevent EMI. The camera may output image signals in a digital format, or in an analog format, depending on the particular camera.

5) High Fidelity Audio headphone 312 with digital/analog microphone: These headphone system are commercially available, such as the Slick non-magnetic devices. This construction produces quality sound and fits all head coils.

6) High Resolution Video Glasses 314: Virtual reality video visor with all non-magnetic display and optics. The signal format may be digital, analog or a combination of both, depending on the particular visor.

7) Patient Input Devices 316: MRI compatible input devices such as mouse, trackball, joystick, touchpad, key pad or other transducer to measure force, temperature, or any other feedback device. These devices typically employ USB signal protocols, but other signal interfaces may also be employed.

8) MRI compatible piezo speakers 316 to allow audible sounds to be reproduced in the magnet room. These speakers are typically driven by analog signals.

9) MRI compatible miniature high-speed eye tracking camera 318 for tracking the eye movements of the patient. The camera 318 may output video signals in a digital or an analog format, depending on the particular camera.

These exemplary devices all need to be interfaced for signal communication with devices in the control room. The magnet room devices are driven or controlled by, or provide different signal formats or protocols. For example, the HDTV may be configured for HDMI (the High Definition Multimedia Interface) signals or DVI signals.

Figure 5:
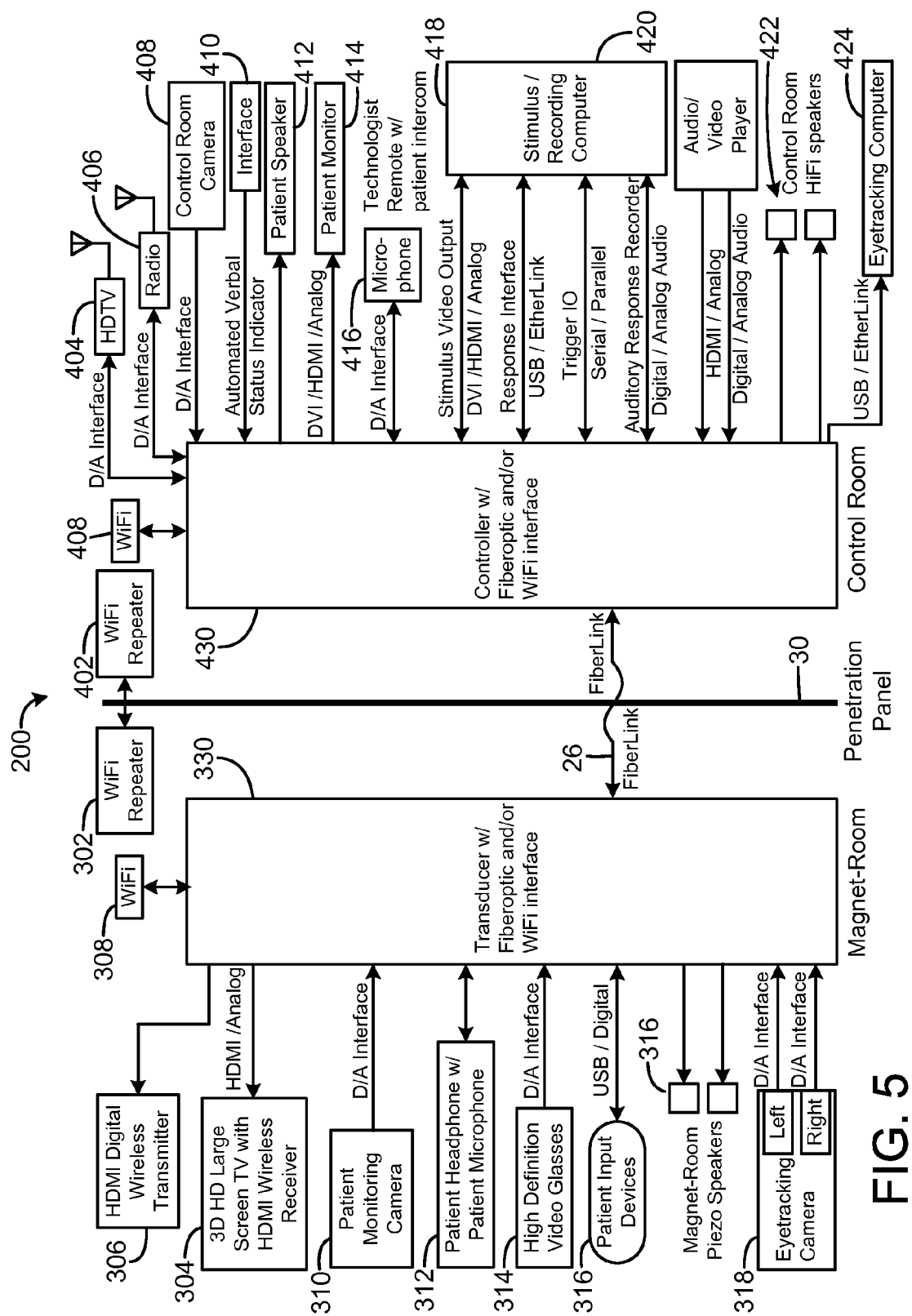
FIG. 5 is a diagrammatic block diagram illustrating features of an exemplary embodiment of an interface system for MRI applications.
Figure 6:
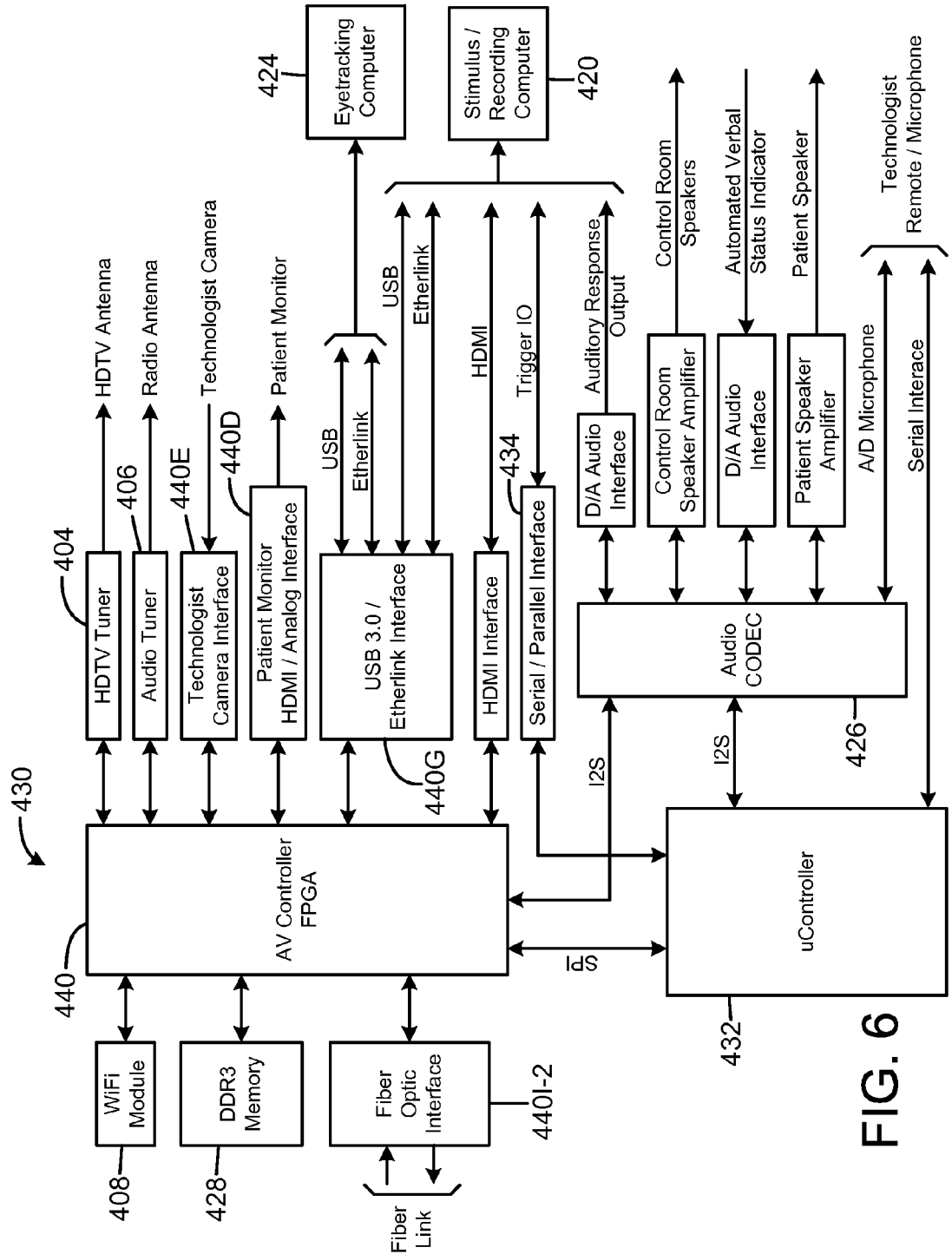
FIG. 6 is a simplified block diagram of an exemplary embodiment of a control room controller system of the interface system as shown in FIG. 5.

B. Control Room Devices:

In the exemplary embodiment illustrated in FIG. 5, the system includes several exemplary devices in the control room, which are connected to the controller 430:

1. HDTV 404.
2. Radio 406.
3. Control Room Camera 408.
4. Interface 410 for Automated Verbal announcer commands generated from the MRI scanner. Status Indicator: MRI generated verbal progress report relayed to the subject while going through the scanning, for example "Hold your breath". This can also allow MRI generated verbal progress reports to be relayed to the patient while going through the scanning, and inform the patient of the test status, e.g. when the battery of tests will be completed.

5. Patient Speaker 412.
6. Patient Monitor 414.
7. Technologist Remote Control 416.
8. Stimulus/patient response recording computer 418.
9. Audio/Video Player 20.
10. Control Room speakers 422.
11. Eye Tracking Computer 424.

The control room devices provide signals of different interface specifications or protocols as indicated in FIG. 5.

The interface system 200 includes a transducer system or module 330 disposed in the magnet room. The transducer system provides a signal interface between the magnet room devices and the control room, and is connected to the Wi-Fi transceiver 302 in the magnet room, and to the devices described above. In an exemplary embodiment, the transducer 330 is implemented with an FPGA, to provide a highly integrated device with high speed serialization/de-serialization modules operating, in this embodiment, at 10 Gbps. The detailed operation of each functional block within the FPGA is defined by a set of registers specific to the functional block. An embedded microcontroller in the transducer configures these registers upon power up and during operation. A functional description of the transducer, referring to FIGS. 8 and 9, follows:

Input/output data processor 340A: This block packs data received from the camera interface, Audio processor (patient microphone), PCIe interface (user interface devices (mouse, keypad, etc. . . . ) and system status into a single stream of data and transfers it to the 8b/10b encoding. Similarly, it unpacks video data (DVD, PC images, etc. . . . ), Audio data (DVD, technologist microphone, etc. . . . ) received from either wireless or optical link which are decoded by 8b/10b decoder into parallel format and transfers them to system status registers, PCIe interface, Video or Audio processor.

Video processor 340B: This Block reconstructs received video timing and formats data output. It scales, mirror and rotates each video frame based on its configuration register's setting. It receives video from controller side through the fiber optic or Wi-Fi link, decompresses and rebuilds the timing associated with video signal. It has the ability to scale, flip, and mirror the image on command. It also features picture-in-picture, on-screen-display which enhances the systems application. When used with the high resolution video glasses, it serializes the video data received from two different sources and transmits them to the video glasses, enabling stereo image display.

8b/10b Encoder/Decoder 340C: 8b/10b is a line code that maps 8 bits of data to 10 bits of data to achieve a DC balance and bounded disparity, and yet provide enough state changes to allow reasonable clock recover. This means that the difference between the count of 1s and 0s in a string of at least 20 bits is no more than 2, and that there are not more than five 1s or 0s in a row. This helps to reduce the demand for the lower bandwidth limit of the channel necessary to transfer the signal. This method is commonly used when transmitting serial data over fiber optic, wireless, etc. mediums.

Serializer/De-Serializer (SerDes): The SerDes interfaces 340D1 (WiFi interface) and 340D2 (fiber optic interface), with switch 340E selecting the data transmission channel, modulates the carrier frequency with the encoded transmitter data. Similarly, it de-modulates received data and extracts and synchronizes the stream to the reference clock.

Audio Processor Interface 340F: This block reconstructs the received audio data into AES data format and timing specifications. Similarly, it embeds the timing of the AES data and transfers it to Data processor.

USB 3.0 interface 340G: Has a built in PCI express interface which enables high speed data transfers (3.2 Gbps) to/from USB 3.0 transceiver device.

Digital Video output 340H: RGB data output with control signals needed to interface with HDMI and analog video circuits in case of failure with Wi-Fi or fiber optics.

Eye Tracking Camera 340I: it processes serial/parallel data received from the eye tracking camera, then synchronizes and timestamps frames for processing. Data is serialized and transferred via fiber link or Wi-Fi link to the AV controller in the control room.

DDR3 Memory interface 340J: This supports the video features described above.

Audio CODEC: This function converts digital audio to analog or analog to digital via its DACs or ADCs and also incorporates a digital microphone interface. The function provides digital audio filters used for out of band noise suppression and anti-aliasing.

Active Noise Cancellation module: This module is highly adaptive to MRI gradient and RF audio noise produced during different MRI test protocols. This module removes mentioned noise from patient voice and audio in headphone.

Video Glasses Interface: The interface receives video via its high speed SerDes modules, decompresses, gamma corrects the data and transfers it to the video glasses.

The AV Controller 430 in the controller room includes the AV Controller FPGA, to provide a highly integrated device with high speed serialization/de-serialization modules operating at 10 Gbps. A functional description of the AV controller, referring to FIGS. 6 and 7, follows:

A. Audio: Audio inputs from external sources, e.g. the technologist's microphone, and a radio tuner, can be either in analog or digital form. The audio CODEC 426 converts these inputs to I2S format, and the audio stream is transferred to the AV controller FPGA 440 for transmission to the transducer in the magnet room. Similarly, signals from the patient microphone in the magnet room are received from the transducer in I2s format, and after appropriate filtering and amplification are output through the patient speaker or as a standard audio signal form recording and post processing.

B. Video: The system has multiple video inputs with different video standards. These inputs are from external video sources, such as a TV tuner 404, DVD player and the technologist video camera. These inputs are converted to digital format, and encoded by the FPGA for transmission to the transducer.

C. USB 3.0 Interface 440G: The system has a built in PCI express interface which enables high speed data transfers, e.g. at 3.2 Gbps, to/from the USB 3.0 transceiver device. A user interface resides on the stimulus/recording computer 418, e.g. a PC or Apple MAC, where system operation can be tailored to the user's requirements with the ability of memorizing different setups for a number of users. This communication port is also used for the eyetracking computer 424, where the subject's eye movements are tracked and recorded.

D. Trigger inputs and outputs with serial/parallel interface 434: External triggers in digital form are accepted by the system for conditioning or action. It also provides trigger outputs to the stimulus computer via a serial or parallel port.

E. Technologist remote control: is a user's interface with features such as communication with subject, volume adjustment and video/audio input selection provided for quick access. A remote control may be provided which is equipped with a display for display of system information.

F. Microcontroller 432: The device manages the system operation, transducer and technologist remote control communications, system power up, initialization sequence and monitoring, and user's interface. It also manages component failure detection, alarm and system operation history recording feature.

G. DDR3 Memory interface 440C and memory 428: This supports the video features explained above.

H. Fiber Optic module interface 440I2: Video/Audio/Commands may be sent and received via an optical fiber link, with a 10 Gbps SerDes module where compressed data is further encoded/decoded via a 10b/8b scheme.

Figure 7:
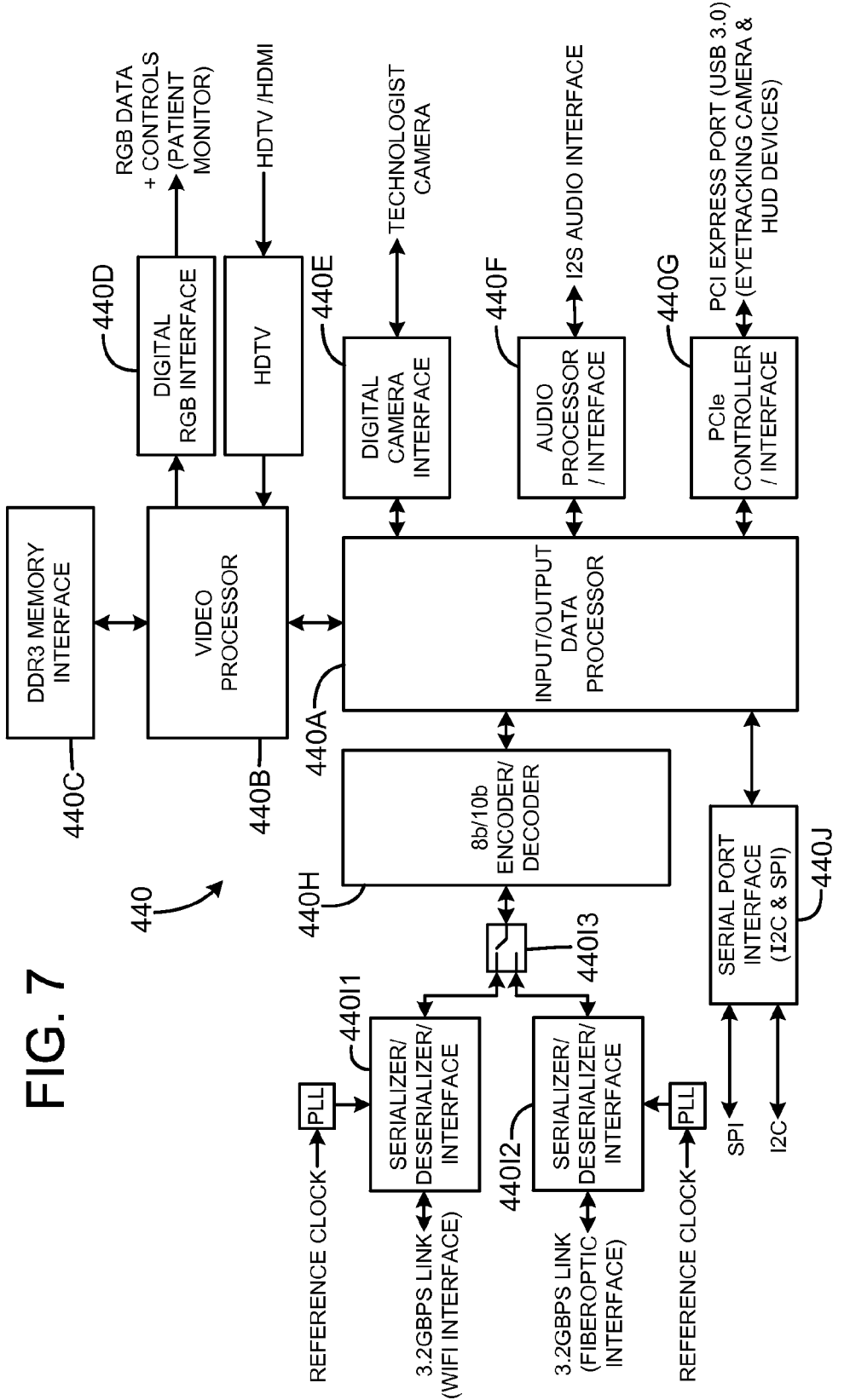
FIG. 7 is a simplified internal block diagram of an exemplary embodiment of the audio/visual (AV) controller of the controller system of FIG. 6, implemented as a field programmable gate array (FPGA).
Figure 8:
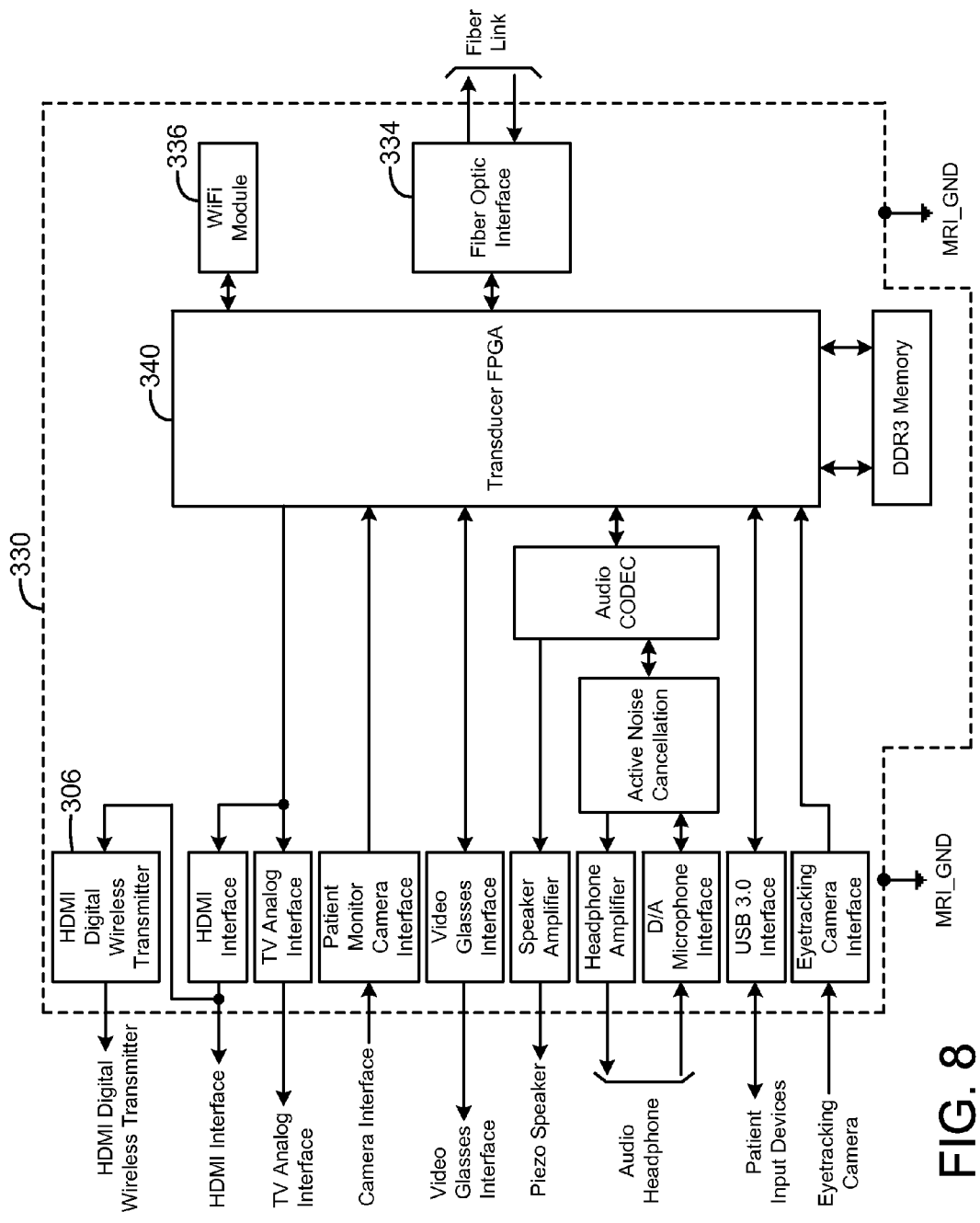
FIG. 8 is a simplified block diagram illustrating features of an exemplary embodiment of the transducer system in the magnet room of the interface system of FIG. 5.
Figure 9:
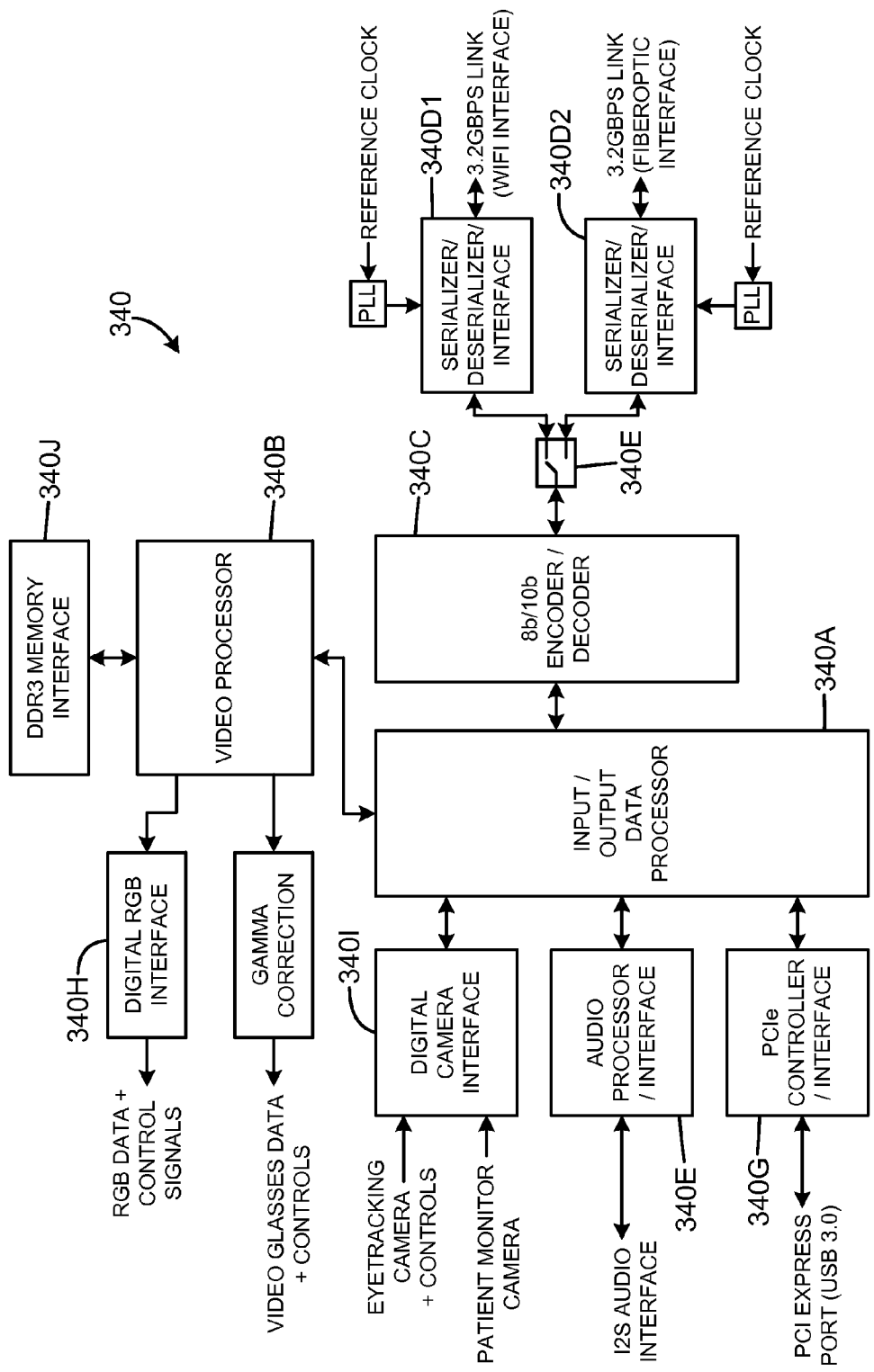
FIG. 9 is a simplified internal block diagram of an exemplary embodiment of the transducer of FIG. 8, implemented as a FPGA.

The AV Controller 430 in this exemplary embodiment includes an FPGA 440. FIG. 7 shows various function blocks implemented by the FPGA and AV controller. The FPGA functions are executed simultaneously in parallel in this exemplary embodiment. The detailed operation of each functional block within the FPGA is defined by a set of registers specific to the functional block. An embedded microcontroller 432 in the AV controller configures these registers upon power up and during operation.

Input/output (I/O) data processor 440A: This function is configured to pack data received from the video processor 440B, the audio processor 440F (DVD, technologist microphone, etc.), PCIe interface, serial port interface and system status into a single stream of data and transfers it to the 8b/10b encoding. Similarly, it unpacks video data (Patient Camera) and audio data (patient microphone) received from either the wireless or the optical link which are decoded by 8b/10b decoder into parallel format and transfers them to system status registers, PCIe interface, the video or audio processor as the case may be.

Video processor 440B: This function reconstructs received video timing and formats the data output. Similarly, it converts the HDTV/HDMI data into a parallel format and transfers it to the I/O data processor block 8b/10b Encoder/Decoder 440H: 8b/10b is a line code that maps 8 bits of data to 10 bits of data to achieve a DC balance and bounded disparity, and yet provide enough state changes to allow reasonable clock recover. This means that the difference between the count of 1s and 0s in a string of at least 20 bits is no more than 2, and that there are not more than five 1s or 0s in a row. This helps to reduce the demand for the lower bandwidth limit of the channel necessary to transfer the signal. This method is commonly used when transmitting serial data over fiber optic, wireless, etc. mediums.

Serializer/De-Serializer (SerDes) (440I1 for the WiFi interface, 440I2 for the fiber optic interface, with a switch 440I3 selecting the signal transmission channel). In an exemplary embodiment, the switch 440I3 is controlled by logic internal to the FPGA of the AV controller 440. The SerDes function block modulates the carrier frequency with the encode transmitter data. Similarly, it de-modulates received data and extracts and synchronizes the stream to the reference clock.

Audio Processor Interface 440F: This block reconstructs the received audio data into AES data format and timing specifications. Similarly, it embeds the timing of the AES data and transfers it to the data processor.

Figure 10:
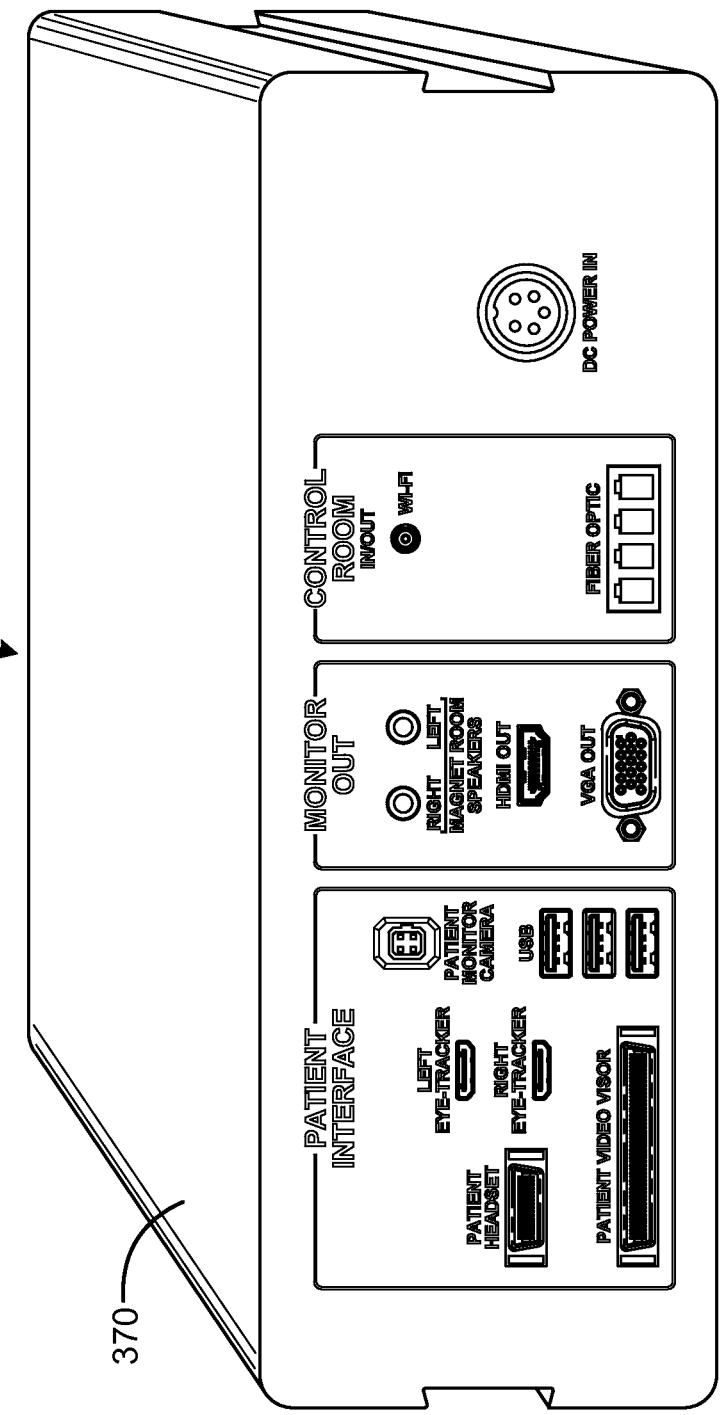
FIG. 10 is a diagrammatic illustration of an exemplary magnet room transducer module with a housing structure.

The magnet room transducer 330 and the control room AV controller 430 are each preferably configured, in exemplary embodiments, as modules housed within housing structures to which are fitted connectors for electrically or optically connecting each of the respective devices. FIG. 10 is a diagrammatic illustration of an exemplary module 330 with a housing structure 370, which houses the circuitry which implements the functions described above. The housing structure 370 physically supports the connectors provided for the various magnet room devices for the patient interface, e.g. for the patient headset, left and right eye-trackers, patient video visor, patient monitor camera, and USB ports. The connectors include connectors grouped as "Monitor Out" connectors, for the magnet room audio speakers, the video output on an HDMI connector and a VGA out connector. The patient video visor connector in this exemplary embodiment is a Molex 12X latch connector; the patient headset connector is a Molex 4X latch connector. Control room input/output WiFI and fiber optic connectors are provided to provide signal connections to WiFi and fiber optic signal transmission links to the control room interface module 430. The connector types are exemplary; other types may be employed.

Figure 11:
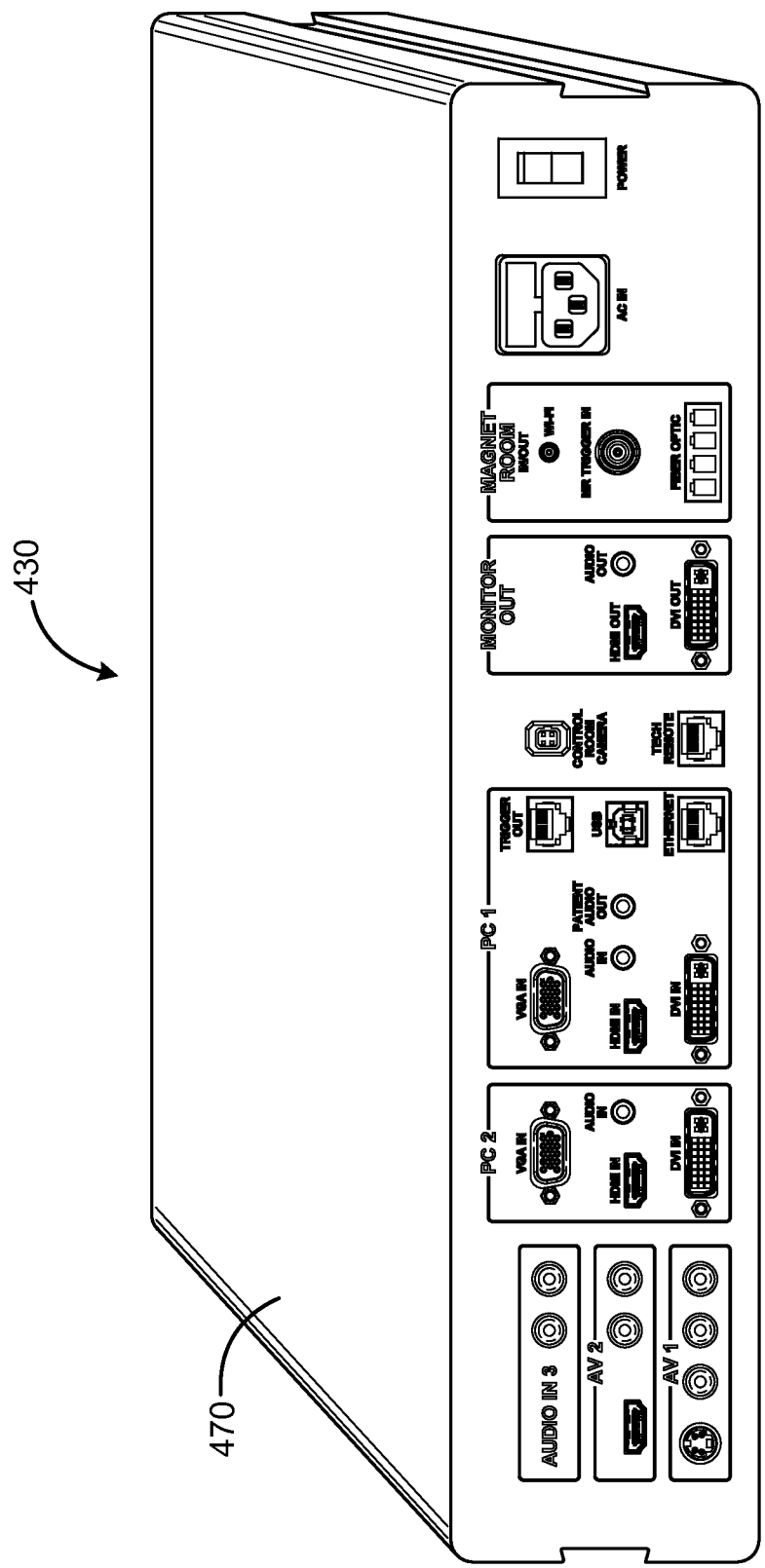
FIG. 11 shows an exemplary embodiment of a physical housing structure for the control room controller module.

FIG. 11 shows an exemplary embodiment of a physical housing structure 470 for the control room controller 430, which physically supports electrical and fiber optic connectors, and houses the circuitry which implements the functions described above. The connectors are labeled in FIG. 11, and include connectors to connect to the WiFI transceiver and the fiber optic transceiver for communication with the transducer 330 in the magnet room. The different connector/interface devices shown in FIG. 11, include, for an exemplary embodiment, RCA connectors for "Audio In 3," RCA and HDMI connectors for "AV2," RCA and DIN connectors for "AV1." The "MR Trigger IN" port receives synchronous pulses generated by MRI to show the start of the Scan and the data connection begins from the patient. In the functional MRI application the user needs to sync the data collection with the MRI scan.

As illustrated in FIGS. 5-11, the interface system provides a system which allows interfacing to different devices in the magnet room and in the control room in self-contained modules.

Although the foregoing has been a description and illustration of specific embodiments of the subject matter, various modifications and changes thereto can be made by persons skilled in the art without departing from the scope and spirit of the invention.

What is claimed is:

1. A universal interface system for interfacing between the outside environment and an MRI (magnetic resonance imaging) magnet room, configured to avow communication between the outside environment and different devices in the magnet room, which devices employ different signal interfaces or signal protocols from others of the devices, the interface system comprising:

a high speed digital data signal transmission link between the MRI magnet room and a control room outside the MRI magnet room;

a signal transducer system module disposed within the magnet room, the signal transducer system module configured for communication with the digital data signal transmission link, and comprising a plurality of transducer connectors configured to connect to corresponding device connectors of a set of the different devices which employ different signal interfaces or signal protocols in the magnet room;

said transducer system module includes a transducer housing mounting said transducer connectors on a housing surface;

the signal transducer system module configured to translate digital signals received through the digital data signal transmission link into signals delivered through at least some of said plurality of connectors of corresponding different formats or protocols for corresponding ones of said different devices in the magnet room, the signal transducer system module further configured to translate signals received through at least some of the transducer connectors from one or more of the corresponding different devices in the magnet room into digital signals for transmission over the digital data transmission link;

a controller system module disposed in the control in signal communication with the high speed digital data transmission link, the controller system module having a plurality of module connectors configured to connect to control room device connectors associated with a plurality of different external devices in the control room, the plurality of control room different devices arranged to deliver video, audio, status or control signals for utilization by one or more of the magnet room devices and which employ different signal interfaces or signal protocols, said plurality of different external devices including a control room computer for controlling patient stimulus and recording patient responses, and said plurality of module connectors including a computer connector for signal connection to the control room computer;

said controller system module including a controller housing mounting said controller connectors on a controller housing surface;

the controller system module configured to translate signals received through at least some of the controller connectors from one or more of the corresponding control room external devices into digital signals for transmission over the digital data transmission link to said transducer system, the control system module comprising an audio codec for converting digital and analog signals received at one or more module connectors from one or more of said external devices into a processed audio codec signal, and a video processor responsive to video data signals received at one or more module connectors for formatting said video data signals into processor video signals having a video predetermined digital format, and is further configured to translate digital signals received through the digital data signal transmission link from the transducer system into signals delivered through at least some of said plurality of controller electrical connectors of a corresponding format and protocol for corresponding ones of said control room external devices.

2. The system of claim 1, wherein the devices in the magnet room include a plurality of different devices selected from the group including a patient monitoring camera, audio headphones for the patient, a patient input device, an audio speaker, a patient eye-tracking camera, and a television.

3. The system of claim 1, wherein the plurality of external devices in the control room include a patient speaker, a patient monitor, a technologist remote control, an audio-video player and an eye tracking computer.

4. The system of claim 1, wherein the signal transducer system disposed within the magnet room comprises an input/output data processor configured to pack data received from the different devices in the magnet room into a single stream of data and transfers the data to a data encoding function for subsequent transmission over the digital data signal transmission link, and to unpack decoded video and audio data received from the digital data signal transmission link into a parallel format.

5. The system of claim 1, wherein the digital data signal transmission link is a wireless local area network.

6. The system of claim 1, wherein the digital data signal transmission link includes an optical fiber digital data transmission link.

7. The system of claim 1, wherein:

the controller system module further includes a data encoder-decoder and an input/output (I/O) data processor responsive to the video processor signals and the audio codec signals to pack said respective signals corresponding to video and audio data received from different devices in the outside environment into a single stream of data and to transfer the stream of data to the data encoder-decoder for subsequent transmission over the digital data signal transmission link.

8. The system of claim 1, wherein the digital data signal transmission link includes a wireless local area network and an optical fiber data transmission link, and the controller system module includes a first switch for switching signal transmission between the wireless local area network and the optical data transmission link, and the transducer system module includes a second switch for switching signal transmission between the wireless local area network and the optical data transmission link, the first switch and the second switch operable to select either said wireless local area network or said optical fiber data transmission link for operation to transfer data and signals between the signal transducer system module and the controller system module.

9. An interface system for providing a signal interface between devices in a magnetic resonance imaging (MRI) magnet room and devices in the outside environment to the magnet room, which devices employ different signal interfaces or signal protocols from others of the devices, comprising:

a signal transmission link between the MR magnet room and the outside environment, the link including a wireless local area network;

a controller system located in the outside environment and connected to the devices in the outside environment, and to the signal transmission link, the controller system including a controller housing structure to which are fitted different connectors for electrically or optically connecting to connectors for different external devices in the outside environment, and which different external devices employ different signal interfaces or signal protocols, the plurality of different external devices including a computer for controlling patient stimulus and recording patent responses, and said different connectors including a computer connector for signal connection to the computer;

a transducer system located in the MRI magnet room and connected to the devices in the MRI magnet room, the transducer system including a transducer housing structure to which are fitted different connectors for electrically or optically connecting to connectors for each of the devices in the magnet room which employ different signal interfaces or signal protocols;

the controller system comprising an audio codec for converting digital and analog audio signals received at one or more module connectors from one or more of said external devices into a processed audio digital signal, and a video processor responsive to video data signals received at one or more module connectors for formatting said video data signals into video processor signals having a video predetermined digital format, and is further configured to translate digital signals received through the digital data signal transmission link from the transducer system into signals delivered through at least some of said plurality of controller electrical connectors of a corresponding format and protocol for corresponding ones of said different external devices; and wherein the controller system and the transducer system are each self-contained modules within the respective controller housing structure and the transducer housing structure.

10. The system of claim 9, wherein the devices in the magnet room include a plurality of different devices selected from the group including a patient monitoring camera, audio headphones for the patient, a patient input device, an audio speaker, a patient eye-tracking camera, and a television.

11. The system of claim 9, wherein the plurality of different external devices in the outside environment include a patient speaker, a patient monitor, a technologist remote control, an audio-video player, a control room speaker and an eye tracking computer.

12. The system of claim 9, wherein the signal transducer system comprises an input/output data processor configured to pack data received from the different devices in the magnet room into a single stream of data and transfers the data to a data encoding function for subsequent transmission over the digital data signal transmission link, and to unpack decoded video and audio data received from the digital data signal transmission link into a parallel format.

13. The system of claim 9, wherein the controller system comprises an input/output (I/O) data processor responsive to the video processor signals and the audio codec signals to pack data received from the different devices in the outside environment into a single stream of data for transmission over the digital data signal transmission link.

14. The system of claim 9, wherein the signal transmission link further includes an optical fiber data transmission link, and the controller system includes a first switch for switching signal transmission between the wireless local area network and the optical data transmission link, and the transducer system includes a second switch for switching signal transmission between the wireless local area network and the optical data transmission link, the first switch and the second switch operable to select either said wireless local area network or said optical fiber data transmission link for operation to transfer signals between the transducer system and the controller system module, thereby providing a redundant or backup signal transmission link for the system.

15. The system of claim 9, wherein the transducer system includes a video processor configured to convert signals from the signal transmission link into video signals for a display in the magnet room, and an audio processor configured to convert signals from the signal transmission link into audio signals for an audio headphone or speaker system in the magnet room.

* * * * *